(12) United States Patent
Nir et al.

(10) Patent No.: US 12,183,038 B2
(45) Date of Patent: Dec. 31, 2024

(54) CAMERA CALIBRATION USING FIDUCIAL MARKERS ON SURGICAL TOOLS

(71) Applicant: Asensus Surgical Europe Sàrl, Bertrange (LU)

(72) Inventors: Tal Nir, Durham, NC (US); Lior Alpert, Durham, NC (US)

(73) Assignee: Asensus Surgical Europe Sàrl, Bertrange (LU)

( * ) Notice: Subject to any disclaimer, the term of this patent is extended or adjusted under 35 U.S.C. 154(b) by 0 days.

(21) Appl. No.: 17/495,784

(22) Filed: Oct. 6, 2021

(65) Prior Publication Data

US 2022/0108475 A1 Apr. 7, 2022

Related U.S. Application Data

(60) Provisional application No. 63/088,414, filed on Oct. 6, 2020.

(51) Int. Cl.
*A61B 5/107* (2006.01)
*A61B 1/313* (2006.01)
*A61B 90/00* (2016.01)
*G06T 7/80* (2017.01)

(52) U.S. Cl.
CPC .............. *G06T 7/80* (2017.01); *A61B 1/3132* (2013.01); *A61B 90/39* (2016.02); *A61B 2090/3937* (2016.02); *G06T 2207/10068* (2013.01); *G06T 2207/30004* (2013.01); *G06T 2207/30204* (2013.01)

(58) Field of Classification Search
CPC ............. G06T 7/80; G06T 2207/10068; G06T 2207/30004; G06T 2207/30204; A61B 90/39; A61B 1/3132; A61B 2090/3937
See application file for complete search history.

(56) References Cited

U.S. PATENT DOCUMENTS

| | | | | |
|---|---|---|---|---|
| 6,165,181 | A * | 12/2000 | Heilbrun | G06T 7/33 348/E13.016 |
| 2006/0004286 | A1* | 1/2006 | Chang | A61B 90/16 606/198 |
| 2007/0208252 | A1* | 9/2007 | Makower | A61B 6/032 606/198 |
| 2012/0259204 | A1* | 10/2012 | Carrat | A61B 34/20 600/414 |
| 2017/0119474 | A1* | 5/2017 | Kronman | A61B 1/00006 |
| 2017/0273665 | A1* | 9/2017 | Kapoor | A61B 6/12 |
| 2020/0034969 | A1* | 1/2020 | Isaacs | A61B 90/96 |
| 2022/0108475 | A1* | 4/2022 | Nir | A61B 1/00057 |

FOREIGN PATENT DOCUMENTS

WO WO-2013177051 A1 * 11/2013 ............. A61B 34/10

* cited by examiner

*Primary Examiner* — Zaihan Jiang

(57) ABSTRACT

Calibration of parameters of an endoscopic or laparoscopic camera is conducted while the camera is in use capturing images of a surgical procedure at a surgical site. The surgical procedure is performed using a surgical instrument marked with a fiducial pattern. A processor receives image data from images captured by the camera and uses machine vision to detect points of the pattern, and carries out an optimization to determine the 3D pose of the surgical instrument relative to the camera and the camera parameters.

22 Claims, 3 Drawing Sheets

CAMERA CALIBRATION USING FIDUCIAL MARKERS ON SURGICAL TOOLS

BACKGROUND

Computer vision can be a useful tool for gaining an understanding of a surgical environment. For example, it can be used to estimate 3D measurements between features within an operative site, such as the measurements between instruments disposed at the surgical site, or measurements of anatomical features within the body cavity. Co-pending and commonly owned U.S. application Ser. No. 17/035,534, entitled "Method and System for Providing Real Time Surgical Site Measurements" describes a system and method that use image processing of the endoscopic view to determine sizing and measurement information for a hernia defect or other area of interest within a surgical site. Co-pending and commonly owned U.S. application Ser. No. 17/099,761, entitled "Method and System for Providing Surgical Site Measurements" describes a system and method that use image processing of images of the endoscopic view to estimate or determine distance measurements between identified measurement points at the treatment site. The measurements may be straight line point to point measurements, or measurements that follow the 3D topography of the tissue positioned between the measurement points.

Camera calibration is essential for such physical 3D measurements using image data, and for other computer vision features such as image distortion correction, image rectification, etc.

Camera calibration solutions typically involve some unique known patterns (fiducials) presented in front of the camera in different poses. A commonly used technique is similar to that described in Z. Zhang, "A flexible new technique for camera calibration," in *IEEE Transactions on Pattern Analysis and Machine Intelligence*, vol. 22, no. 11, pp. 1330-1334, November 2000 ("Zhang"). This type of calibration works well but depending on the context in which the camera is to be used, it can delay use of the camera, occupy personnel, and make it difficult to perform "on the fly" calibrations. A camera calibration procedure typically involves printing a checkerboard grid on a planar surface, or using some other designed fiducials, and moving the camera in front of the pattern, or vice versa. However, in the operating room, calibrating a laparoscopic camera before surgery is a time consuming task that adds to the burden of the operating room staff before surgery. Also adding the equipment (fiducials) to the operating room takes from the typically limited available space.

In robotic surgery and in manual laparoscopic surgical procedures a camera (e.g., an endoscopic/laparoscopic camera) is positioned in a body cavity to capture images of a surgical site. It would be advantageous to calibrate the camera on the fly without occupying the operating room staff with the time-consuming calibration task, and with having to hold a calibration pattern in front of the camera in the operating room prior to commencing the procedure.

This application describes the use of fiducials/markers on the operating tools in order to gather the data required for camera calibration, both for monocular and stereo vision cameras.

DETAILED DESCRIPTION

Figure 1:
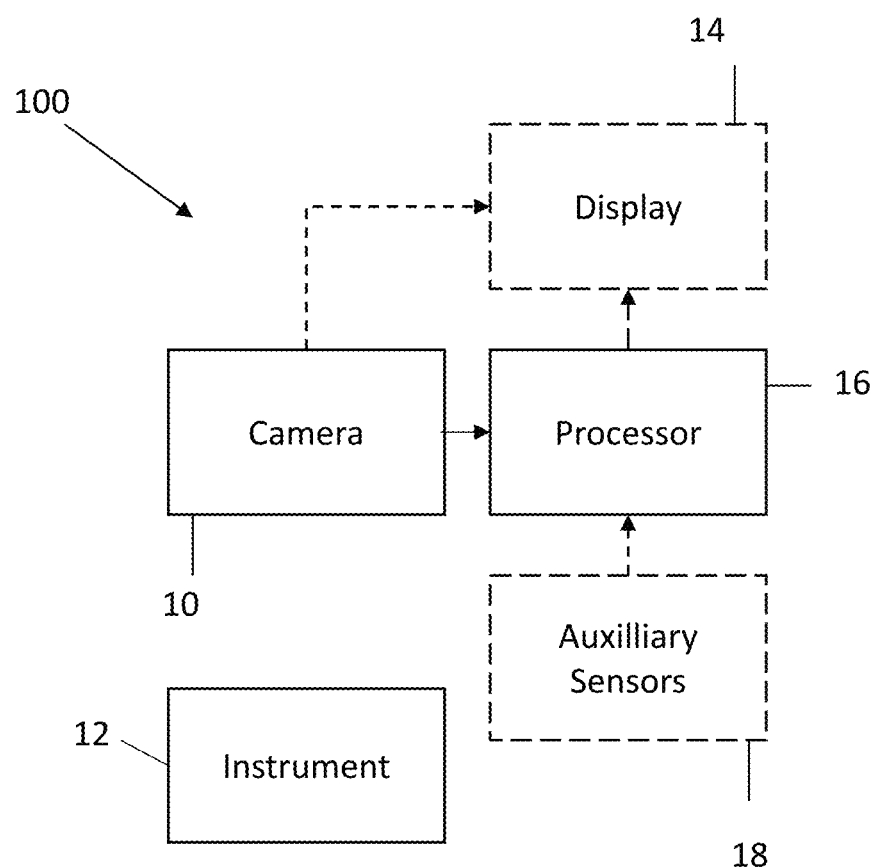
FIG. 1 is a block diagram of an exemplary calibration system.

This application describes a system that calibrates an endoscopic/laparoscopic camera during use of that camera in a surgical procedure. Referring to FIG. 1, the system 100 comprises a camera 10, which may be any laparoscopic/endoscopic camera used during surgery. It may be a stereo camera or a monocular camera. In the methods described in this application, this camera is the subject of the calibration procedure.

The system further includes one or more surgical tools or instruments 12 positionable at the surgical treatment site such that they are within the field of view of the camera 10. These surgical instruments are a type configured to be manually- or robotically-maneuvered within a patient's body cavity for the purpose of performing a therapeutic or diagnostic procedure. The tools may have operative ends with end effectors such as jaws, hooks, needles, electrosurgical elements, diagnostic elements, electrodes, blades, ultrasound transducers, lasers, fiber optics, sensors, suction, irrigation or insufflation features, or any other features suitable for performing or facilitating diagnostic or therapeutic steps at the surgical site.

Figure 2:
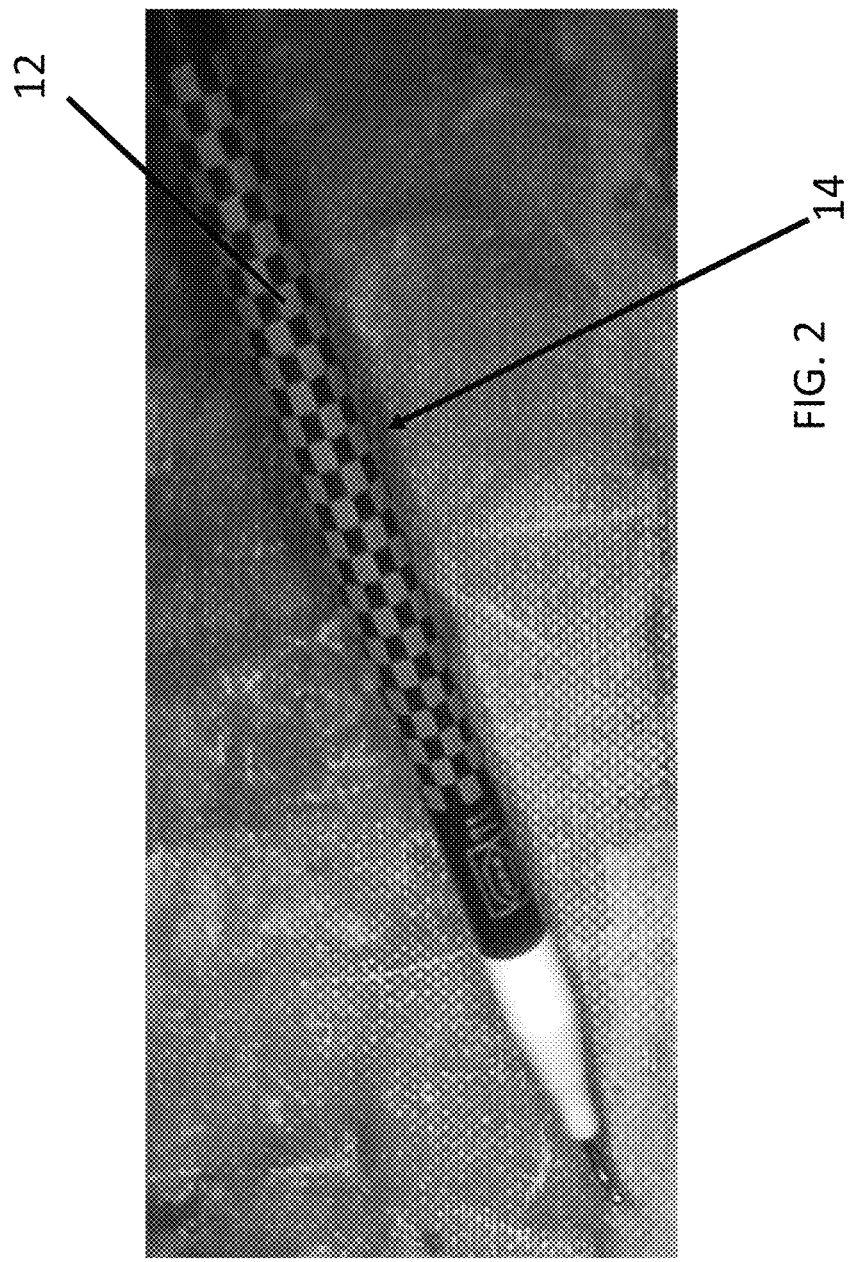
FIG. 2 shows a display of an image of a surgical site at which a surgical instrument having fiducial markers is positioned.

Referring to FIG. 2, the tools are marked by some fiducials 14 designed for the calibration procedure, e.g., checkerboard pattern, circles, etc. The fiducials have known geometric properties, size, spacing, etc. These markings can be applied to the instruments by deposition or coating, coloring, laser marking, etching, etc. In preferred embodiments, the patterns of fiducials extend fully 360 degrees around the surface of the instrument shaft, although in some embodiments they may extend less than fully around the instrument shaft. In other embodiments, the patterns extend 180 degrees or less around the surface of the instrument shaft. These fiducials can be identified during the operation and used during the course of a surgical procedure to calibrate the camera while the instruments are being used at the surgical site to perform therapeutic treatments or diagnostic steps.

In the embodiment shown in FIG. 1, the instrument includes a checkerboard pattern of fiducials created using laser marking techniques of the type used to mark text onto instruments. In this embodiment, the fiducials are on a cylindrical portion of the tool shaft. It is preferable that the fiducials be positioned on a uniformly shaped portion of the instrument, such as on a cylindrical shaft. In other embodiments, patterns other than checkboard patterns can be used, including, without limitation, patterns of circles, may alternatively be used, so long as they have a well-defined geometry.

In some embodiments, calibration may be performed while several such marked surgical instruments can be in the field of view. This can accelerate the calibration process due to the presence of additional simultaneous data points.

Referring again to FIG. 1, in most uses of the system the camera 10 generates images that are displayed on an image display 14, although the display is optional for the purposes of the disclosed invention.

The system includes at least one processor 16 that receives the images/video from the camera(s) 10. Optional sources of input to the processor may include input from auxiliary sensors 18. If the system is used in robotic surgery, the auxiliary sensors may include one or more sensors of the robotic arm that measure the robotic arm movements or determine camera position using kinematics. Other auxiliary sensors may include inertial measurement units (IMUs) or other sensors that facilitate measurement of camera movement. In some embodiments, auxiliary sensors may include additional digital cameras positioned to capture regions of the pattern of fiducials outside of the field of view of camera 10.

The processor includes at least one memory storing algorithms executable by the processor to perform an optimization that solves for the 3D pose of the tool relative to the camera, along with the camera parameters in a single vector of unknowns constructed for the optimization process, as described below.

In performing the calibration, the processor receives video image data captured by the camera, and samples frames from the video. The image data includes images of the instruments as it moves within the surgical site. The pattern on the tool is detected by standard machine vision tools for pattern detection. Thus, in the example shown in FIG. 3, the scene points identified by the processor may be corners of a checkerboard pattern, which are detected in multiple frames of the images captured with the surgical instrument in various location.

Figure 3:
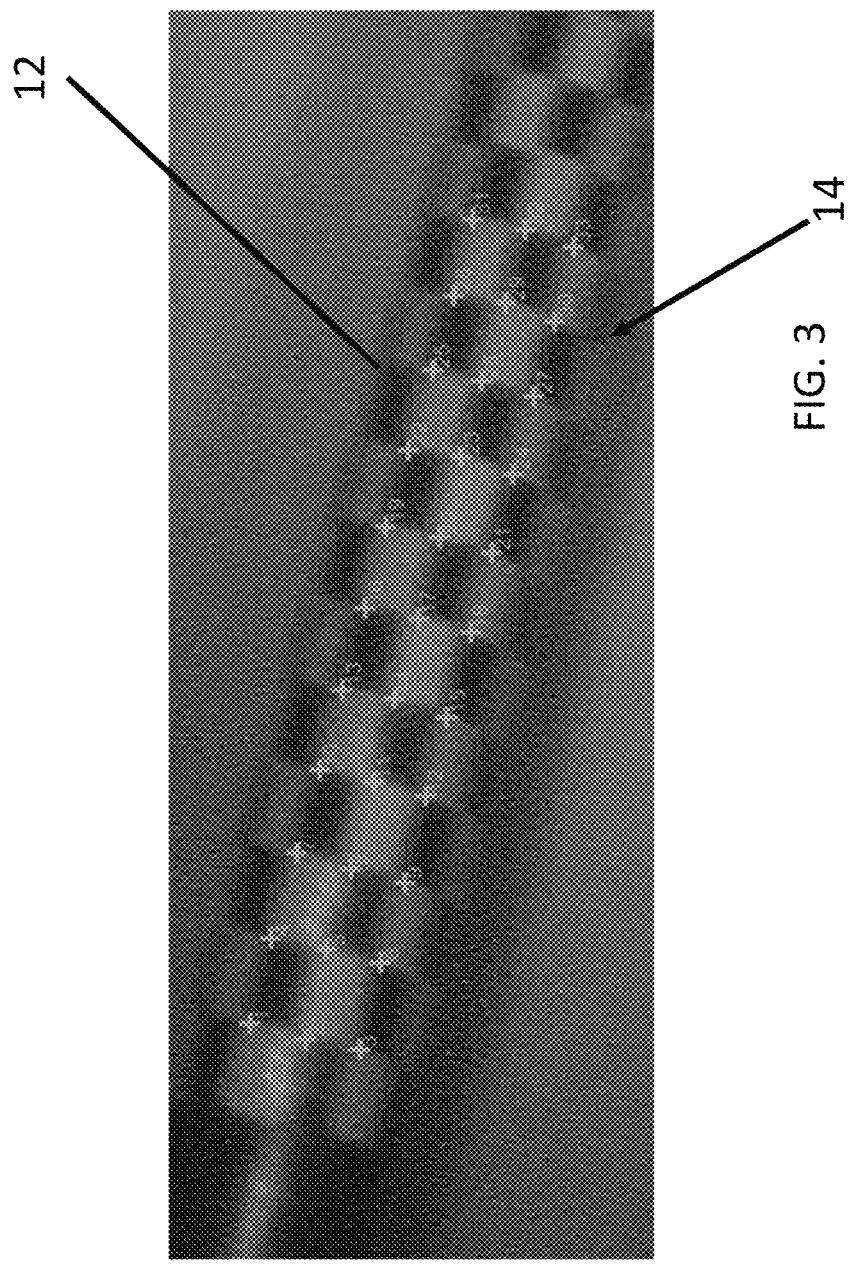
FIG. 3 shows the surgical instrument of FIG. 2 following identification of the fiducial pattern by the system.

FIG. 3 shows an enlarged view of a portion of the instrument shaft of FIG. 2, and further shows the extracted image feature points on the tool (the corners of the pattern), which are marked by a "+" symbol. These image points are ordered by a consistent geometrical order (which in this case is first around, then along the tool). The numbering shown on the image reflects this order, with the corners marked at the left-most column being marked 1, 2 and 3 from top to bottom of the image—corresponding to the circumferential direction around the shaft. The next adjacent is marked 4, 5, 6, etc., with "adjacent" in this discussion meaning adjacent in a longitudinal direction of the shaft. The numbering of the corners in FIG. 3 continues in this way such that the far right column is marked, from top to bottom, 31, 32, and 33.

The processor estimates the camera parameters, using the multi frame sampled image fiducials location, and the known fiducials geometry in order to estimate the camera parameters. The equations in the optimization formulation consider the surface geometry of the surgical tool on which the fiducials are positioned, recognizing that the extracted image feature points are 3D points (on a cylinder in the illustrated embodiments) rather than being on a planar surface as is currently used in the art. Thus, after points on the fiducials are detected, 3D points are constructed accordingly along (longitudinally) and around (circumferentially) a virtual 3D cylinder with the tool's known diameter.

The optimization problem includes the 3D pose of the camera relative to the tool, and the 2D location of the image points (2 images in the case of a stereo camera). Points that are occluded (on the part of the cylinder that is not visible because it faces away from the camera, and points on part of the tool outside the field of view), are not included. The tool's 3D pose can be approximated by triangulation with nominal (approximate) stereo parameters for rough initialization prior to the optimization process The 3D points are projected on the image plane (or the two image planes in the case of a stereo camera) while the optimization is performed, and the camera parameters and the tool's 3D pose are changed. The optimization might minimize the mean reprojection error on all the points/views/cameras, solving for the camera parameters and the 6DOF of the tool relative to the camera pose in each view. The signed reprojection errors on the image plane are used for minimizing the sum of squared errors which provides the camera calibration parameters extracted from the optimized vector of unknowns.

The optimization can be performed by standard nonlinear optimization methods such as Levenberg-Marquardt.

If other sensors are available, these might be used in order to improve the calibration results. A SLAM (simultaneous localization and mapping) approach might also be used.

The estimated camera parameters include the camera intrinsic parameters, focal lengths, camera center, radial distortion parameters, etc. Also, extrinsic parameters can be estimated for a stereo camera, e.g. 6DOF of the relative 3D camera pose. The estimated parameters may be used for radial distortion correction for the image data displayed to the surgical staff on the image display, estimating 3D structure of the scene for a stereo camera, 3D measurement of anatomical features, selected distances, or depths within the surgical site, etc.

Advantages of the disclosed system and method are advantageous in that they do not require a specific calibration stage prior to surgery. Instead, calibration can be done "on the fly" during regular use of the instrument(s) and camera in the performance of a surgical procedure. It does not require user interaction and can therefore be conducted without interruption to the surgery and be seamless to the user. It can adapt to camera/scope changes during surgery, adapting to 0/30/45 deg scopes, monocular or stereo.

What is claimed is:

1. A surgical instrument having a distal portion positionable in a body cavity, the surgical instrument including an elongate shaft and a fiducial calibration pattern for use in estimating intrinsic camera parameters of a stereo endoscopic camera used at the surgical site, the fiducial calibration pattern positioned on the elongate shaft such that the fiducial calibration pattern is disposed within the body cavity and visible to a stereo endoscopic camera capturing images from within said body cavity during a surgical procedure.

2. The surgical instrument of claim 1, wherein the pattern comprises a plurality of polygons of known geometry.

3. The surgical instrument of claim 2, wherein the polygons are rectangles.

4. The surgical instrument of claim 3, wherein the pattern is a checkerboard pattern.

5. The surgical instrument of claim 1, wherein the surgical instrument includes a diagnostic or therapeutic element at a distal end of the shaft.

6. The surgical instrument of claim 1, wherein the fiducial calibration pattern extends 360 degrees around a circumference of the shaft.

7. A method of calibrating a camera during surgery, comprising the steps of:
  positioning a camera with its distal end at a surgical treatment site within a body cavity;
  providing a surgical instrument having a fiducial calibration pattern thereon, and positioning the surgical instrument such that the fiducial calibration pattern is disposed within the body cavity;
  with the distal end of the camera within the body cavity, using the camera to capture a plurality of images of the surgical instrument within the body cavity; and
  based on locations of image fiducials in the plurality of images, and the known fiducials geometry, estimating the camera parameters.

8. The method of claim 7, wherein the fiducial calibration pattern is on the shaft of the instrument.

9. The method of claim 7, further comprising the step of using the surgical instrument to treat tissue at the treatment site while estimating the camera parameters.

10. The method of claim 7, further comprising the step of using the surgical instrument to diagnose a condition at the treatment site while estimating the camera parameters.

11. The method of claim 7, wherein estimating the camera parameters includes estimating the intrinsic camera parameters.

12. The method of claim 7, wherein estimating the camera parameters includes estimating the extrinsic camera parameters.

13. The method of claim 7, further including the step of using the camera to capture a plurality of surgical images of the surgical treatment site within the body cavity and displaying said plurality of surgical images in real time on a display.

14. A surgical system comprising:
- a stereo endoscopic camera positionable in a body cavity;
- a surgical instrument positionable in the body cavity, the surgical instrument including an elongate shaft and a fiducial calibration pattern on the elongate shaft;
- at least one processor comprising at least one memory storing algorithms executable by the processor to:
  - while the stereo endoscopic camera is positioned with its distal tip in the body cavity, receive images from the stereo endoscopic camera, the images comprising images captured from within the body cavity, wherein said images are of the fiducial calibration pattern within the body cavity, and
  - using a location of scene points in the fiducial calibration pattern in a plurality of the images and a known geometry of the fiducial calibration pattern, estimating the parameters of the stereo endoscopic camera.

15. The system of claim 14, wherein the pattern comprises a plurality of polygons of known geometry.

16. The system claim 15, wherein the polygons are rectangles.

17. The system of claim 14, wherein the pattern is a checkerboard pattern.

18. The system of claim 14, wherein the surgical instrument includes a diagnostic or therapeutic element at a distal end of the shaft.

19. The system of claim 14, wherein the fiducial calibration pattern extends 360 degrees around a circumference of the shaft.

20. The system of claim 14, wherein the parameters include intrinsic parameters.

21. The system of claim 14, wherein the parameters include extrinsic parameters.

22. The method of claim 14, wherein the system further includes a display, wherein the camera is further for capturing a plurality of surgical images of a surgical treatment site within the body cavity for display in real time on the display.

* * * * *